United States Patent [19]

Coxon

[11] Patent Number: 4,675,393

[45] Date of Patent: Jun. 23, 1987

[54] PROCESS FOR PREPARING GLUCOSE PENTA-ACETATE AND XYLOSE TETRA-ACETATE

[75] Inventor: Andrew C. Coxon, Wirral, England

[73] Assignee: Lever Brothers Company, New York, N.Y.

[21] Appl. No.: 733,413

[22] Filed: May 13, 1985

Related U.S. Application Data

[63] Continuation of Ser. No. 478,403, Mar. 24, 1983, abandoned.

[30] Foreign Application Priority Data

Apr. 2, 1982 [GB] United Kingdom ................. 8209936

[51] Int. Cl.$^4$ ............................................. C07H 1/00
[52] U.S. Cl. ..................... 536/18.6; 536/119
[58] Field of Search ....................... 536/18.6, 115, 119

[56] References Cited

U.S. PATENT DOCUMENTS

| | | | |
|---|---|---|---|
| 2,013,034 | 9/1935 | Cox et al. ............................ | 536/119 |
| 2,174,541 | 10/1939 | Walthausen et al. ............... | 539/119 |
| 2,376,378 | 5/1945 | Murray ............................... | 536/119 |
| 2,857,378 | 10/1958 | Hales . | |
| 3,824,286 | 7/1974 | Grimmelikhuysen . | |

FOREIGN PATENT DOCUMENTS 133314 12/1974 Japan .

OTHER PUBLICATIONS

Pigman, *The Carbohydrates*, New York: Academic Press Inc., 1957, pp. 139–142, 198–199.
Kirk-Othmer, Encycl. of Chem. Technology, vol. 19, 2nd Ed., John Wiley & Sons, NY (1969), pp. 226–227.
Japanese Patent Application 49/133,314 and what is belived to be an accurate English Translation.

*Primary Examiner*—Johnnie R. Brown
*Assistant Examiner*—Elli Peselev
*Attorney, Agent, or Firm*—James J. Farrell

[57] ABSTRACT

A cost-effective process suitable for the commercial production of the sugar acetate, glucose penta-acetate and xylose tetra-acetate is disclosed. The process comprises a first reaction stage wherein glucose or xylose is partially acetylated with acetic acid to form glucose diacetate or xylose diacetate, followed by a second reaction stage wherein said diacetate product is fully acetylated by treatment with excess acetic anhydride to form glucose penta-acetate or xylose tetra-acetate, respectively. Any excess of acetic anhydride/acetic acid and by-product acetic acid can be recycled for use in the process.

4 Claims, No Drawings

PROCESS FOR PREPARING GLUCOSE PENTA-ACETATE AND XYLOSE TETRA-ACETATE

This is a continuation of Ser. No. 478,403, filed Mar. 24, 1983, now abandoned May 13, 1985.

The acetates of sugars, particularly glucose penta-acetate (GPA) and xylose tetra-acetate (XTA), can be used as suitable activators for percompounds, such as hydrogen peroxide, sodium perborate and sodium percarbonate, functioning by the generation of peroxy acetic acid.

This invention relates to a process for the preparation of the sugar acetates, glucose penta-acetate and xylosetetra-acetate.

Glucose acetate has been prepared by reacting glucose with an acetylating agent, such as acetic anhydride, acetic anhydride/acetic acid mixture or ketene in the presence of a catalyst e.g. sodium acetate, potassium acetate or pyridine sulphuric acid. The currently recommended method for preparing fully acetylated sugars, including glucose, uses acetic anhydride and sodium acetate catalyst (see Kirk Othmer, Encycl. of Chem. Technology, Volume 19, 2nd Ed., John Wiley, New York, 1969, page 26; Japanese Patent Application JP No. 49/133 314).

It has been established that the reaction of D-glucose with excess acetic anhydride and relatively large amounts of anhydrous sodium acetate catalyst (e.g. molar ratio glucose:acetic anhydride:catalyst, 1:10:1) as proposed by previous investigators produces a satisfactory product at reasonably high yields. It was also possible to reduce the acetic anhydride and catalyst levels to a molar ratio glucose:acetic anhydride:catalyst of 1:7.5:0.3. Since both the excess acetic anhydride and the acetic acid formed in these reactions can be recovered, further reduction of the acetic anhydride level would not give a significant cost reduction. For maximum cost-effectiveness it would be necessary to further reduce the level of sodium acetate catalyst (not recoverable) and that of the acetic anhydride to the minimum that would still give glucose penta-acetate of acceptable quality.

Attempts to reduce the anhydrous sodium acetate level further (i.e. below a mole ratio of 1:7.5:0.3) however resulted in crude products which were difficult to crystallize, presumably due to the presence of lower acetates of glucose.

Longer reaction times did not overcome this problem, caused considerable darkening of the reaction mixture and were therefore undesirable.

The above procedure of the art requires at least 5 moles of acetic anhydride to produce 1 mole of glucose penta-acetate and also produces 5 moles of acetic acid by-product. By the same token at least 4 moles of acetic anhydride are required to produce 1 mole of xylose tetra-acetate, thereby producing 4 moles of acetic acid by-product. For said process to be viable, a market would be required for the abundant acetic acid by-product.

It is an object of the present invention to provide a more cost-effective process suitable for the industrial production of the sugar acetates, glucose penta-acetate and xylose tetra-acetate.

The process of the invention utilises acetic acid for an at least partial acetylation of the sugars, glucose or xylose.

The partially acetylated product obtained therefrom i.e. a mixture of glucose acetates or a mixture of xylose acetates containing about 2 acetate units per glucose or xylose molecule, termed hereinafter "glucose diacetate" and "xylose diacetate" respectively, is then fully acetylated in a second acetylation reaction step by treatment with acetic anhydride to produce glucose penta-acetate or xylose tetra-acetate.

It is therefore within the broad concept of the invention to provide a process for the preparation of the sugar acetates, glucose penta-acetate or xylose tetra-acetate, comprising a first reaction stage wherein the sugar, glucose or xylose, is partially acetylated with acetic acid to produce glucose diacetate or xylose diacetate, followed by a second stage of reaction wherein said diacetate product is fully acetylated by treatment with acetic anhydride to produce glucose penta-acetate or xylose tetra-acetate, respectively.

The first stage reaction is carried out at a temperature of between 80° and 120° C., preferably at about 100° C. The second stage reaction is conveniently carried out under reflux at the appropriate temperature.

An acid catalyst e.g. p-toluene sulphonic acid is used in the first stage of the process and an alkali metal acetate, e.g. sodium acetate is used as the catalyst in the second stage, as explained below for the manufacture of glucose penta-acetate and xylose tetra-acetate, respectively.

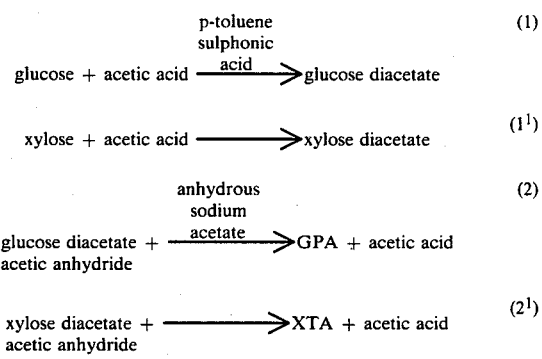

Accordingly the invention provides a process for preparing a sugar acetate, selected from glucose penta-acetate and xylose tetra-acetate, comprising a first reaction stage wherein a sugar, selected from glucose and xylose, is catalytically reacted with acetic acid at a ratio of one mole of sugar to more than 2 moles, preferably about 3 moles, of acetic acid to form a diacetylated product (glucose di-acetate or xylose diacetate), followed by a second reaction stage wherein said diacetylated product is further catalytically reacted with excess acetic anhydride to form the respective glucose penta-acetate or xylose tetra-acetate.

Reactions (1) and (2) starting from glucose

In the presence of 1% p-toluene sulphonic acid catalyst in the first stage it is possible to introduce an average of 1.7 acetates per molecule of glucose by reaction with acetic acid to produce glucose diacetate.

The glucose diacetate is then totally acetylated by treatment with acetic anhydride in the presence of anhydrous sodium acetate. The mole ratio of glucose diacetate:acetic anhydride:anhydrous sodium acetate usable in the second stage is within the range of from about 1:7.5:0.5 to 1:5:0.25, preferably 1:5:0.33.

Further reduction of the glucose diacetate:anhydrous sodium acetate mole ratio below 4:1 is not advisable, since it tends to reduce the efficiency of the acetylation, such that the product would not crystallize.

Reactions (1¹) and (2¹) starting from xylose

In the presence of 1% p-toluene sulphonic acid catalyst in the first stage it is possible to introduce an average of 1.8 acetates per molecule of xylose by reaction with acetic acid to produce xylose diacetate.

The xylose diacetate is then totally acetylated by treatment with acetic anhydride in the presence of anhydrous sodium acetate. The mole ratio of xylose diacetate to acetic anhydride to anhydrous sodium acetate usable in the second stage is within the range of from about 1:7.5:0.5 to about 1:3.3:0.16.

The process of the present invention is more cost-effective than the process of the art in that inexpensive acetic acid is used in the first stage, a lower level of acetic anhydride and sodium acetate can be used, without detrimentally affecting the quality of the sugar acetate, glucose penta-acetate and xylose tetra-acetate, and that the acetic acid generated in the second stage can be recycled for use in the first stage.

EXAMPLE 1

Preparation of glucose penta-acetate

Anhydrous D-glucose (36.0 g=0.20 mole), acetic acid (36.0 g=0.60 mole) and p-toluene sulphonic acid monohydrate (0.36 g=0.002 mole) were heated at 100° C. for 2 hours with stirring. The excess acetic acid and water were removed rapidly under vacuum from the reaction vessel and passed to a separate still for fractionation. The partially acetylated glucose having an average of 1.72 acetyl groups per molecule (50.5 g glucose diacetate) was passed to the second stage reactor together with acetic anhydride and anhydrous sodium acetate catalyst at a mole ratio of 1:5:0.25 and the mixture was heated under reflux with stirring for about 30 minutes. The excess acetic anhydride and acetic acid formed were then rapidly distilled from the reactor and passed to a separate still for fractionation and recycling. The molten product was pumped into a high shear mixer together with water and then passed to a grinder. The product suspension was then filtered and dried in an oven. The yield of glucose diacetate was approximately 85% and all the unreacted acetic acid could be recycled.

The reaction in the second stage was close to quantitative, and 97% of glucose penta-acetate was recovered. All the acetic acid formed and 97% of the unreacted acetic anhydride could be recycled.

EXAMPLE 2

Preparation of xylose tetra-acetate

Anhydrous D(+) xylose (30.0 g=0.20 mole), acetic acid (36.0 g=0.60 mole) and p-toluene sulphonic acid monohydrate (0.36 g=0.002 mole) were heated at about 100° C. for 2 hours with stirring. Unreacted acetic acid and water were then removed rapidly under vacuum from the reaction vessel and passed to a separate still for fractionation and recovery of the acetic acid.

The partially acetylated xylose, having an average of 1.8 acetyl groups per molecule, was passed on to the second stage reactor together with acetic anhydride and anhydrous sodium acetate catalyst at a mole ratio of 1:3.3:0.2 and the mixture was heated under reflux with stirring for about 30 minutes.

The excess of acetic anhydride and acetic acid formed was then rapidly distilled from the reactor and passed to a separate still for fractionation and recycling. The molten product was pumped into a high-shear mixer together with water and then passed to a grinder. The product suspension was then filtered and dried in an oven.

The yield of xylose diacetate was approximately 90% and all the unreacted acetic acid could be recycled.

The reaction in the second stage was close to quantitative. All the acetic acid and about 97% of the unreacted acetic anhydride could be recycled.

I claim:

1. Process for preparing glucose penta-acetate at high yields comprising a first reaction stage wherein glucose is catalytically reacted with acetic acid at a ratio of one mole of glucose to more than 2 moles of acetic acid using p-toluene sulphonic acid as catalyst at a temperature of between 80° C. and 120° C. and removing unreacted acetic acid and water from the reaction mixture to obtain "glucose diacetate", followed by a second reaction stage wherein said glucose diacetate is further catalytically reacted with excess acetic anhydride using sodium acetate as catalyst at a mole ratio of glucose diacetate:acetic anhydride:sodium acetate of about 1:7.5:0.5 to 1:5:0.25 to form glucose penta-acetate.

2. A process according to claim 1, wherein the mole ratio of acetic acid to glucose in the first reaction stage is about 3:1.

3. A process for preparing xylose tetra-acetate at high yields comprising a first reaction stage wherein xylose is catalytically reacted with acetic acid at a ratio of one mole of xylose to more than 2 moles of acetic acid using p-toluene sulphonic acid as catalyst at a temperature of between 80° C. and 120° C. and removing unreacted acetic acid and water from the reaction mixture to obtain "xylose diacetate", followed by a second reaction stage wherein said xylose diacetate is further catalytically reacted with excess acetic anhydride using an sodium acetate as catalyst at a mole ratio of xylose diacetate:acetic anhydride:sodium acetate of about 1:7.5:0.5 to 1:3.3:0.16, to form xylose tetra-acetate.

4. A process according to claim 3, wherein the mole ratio of acetic acid to xylose in the first reaction stage is about 3:1.

* * * * *